(12) United States Patent
Engelhard et al.

(10) Patent No.: US 6,267,895 B1
(45) Date of Patent: *Jul. 31, 2001

(54) CATALYTIC DENTAL WATER APPARATUS

(75) Inventors: Rolf Engelhard; Stephen P. Kasten, both of Prescott, AZ (US)

(73) Assignee: Germiphene Corporation (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/334,484

(22) Filed: Jun. 16, 1999

Related U.S. Application Data (63) Continuation-in-part of application No. 08/648,204, filed on May 14, 1996, now Pat. No. 5,942,125.
(60) Provisional application No. 60/089,541, filed on Jun. 17, 1998.

(51) Int. Cl.[7] ................................. C02F 1/32; C02F 1/78
(52) U.S. Cl. .................. 210/748; 210/760; 210/763; 210/764; 210/221.2; 422/186.3; 433/80
(58) Field of Search ................... 210/748, 760, 210/763, 764, 221.2, 205; 422/186.3; 433/80

(56) References Cited

U.S. PATENT DOCUMENTS

| | | | |
|---|---|---|---|
| D. 357,058 | 4/1995 | Engelhard | D23/209 |
| 2,970,821 | 2/1961 | Axt | 261/16 |
| 3,336,099 | 8/1967 | Czulak et al. | 21/102 |
| 3,550,782 | 12/1970 | Veloz | 210/192 |
| 3,696,932 | 10/1972 | Rosenberg | 210/437 |
| 3,726,404 | 4/1973 | Troglione | 210/139 |
| 4,021,921 | 5/1977 | Detaille | 32/40 R |
| 4,069,153 | 1/1978 | Gunther | 210/64 |
| 4,141,830 | 2/1979 | Last | 210/63 |
| 4,156,652 | 5/1979 | Wiest | 250/527 |
| 4,176,061 | 11/1979 | Stopka | 210/63 |
| 4,179,616 | 12/1979 | Coviello et al. | 250/527 |
| 4,230,571 | 10/1980 | Dadd | 210/760 |

(List continued on next page.)

OTHER PUBLICATIONS

"The Dirty Dental Water Dilemma: A Dentist's Opinion", by Robert A. Silver, *Water Conditioning & Purification*, Sep. 1995, pp. 42–47.

"Dental Waterlines: A Source of Contamination", by J. Williams et al., *Infection Control & Sterilization Technology*, Oct., 1995, pp. 14–20.

(List continued on next page.)

*Primary Examiner*—Chester T. Barry
(74) *Attorney, Agent, or Firm*—Cahill, Sutton & Thomas PLC (57) ABSTRACT

The supply of water used in dental operations and other applications in a dental office, or other medical facility, wherein non-contaminated water is necessary to avoid transmission of microorganisms, is enriched with oxygen, whether from ambient air or a source of oxygen. The oxygenated water is passed through a silver containing catalyst cartridge. The water borne oxygen is attracted to the silver and forms a weak bond sufficient to permit dissociation to oxidize organic matter, including microorganisms. A small amount of silver dissolves in the water and flows downstream through the attendant conduits to and through dental handpieces and dental implements. A portion of the silver will adhere to the walls of the conduits, handpieces and implements where it is free to react with the oxygen dissolved in the water flowing therepast. The resulting oxidizing of the organic matter will destroy any biofilm present and prevent biofilm buildup. To enhance oxidizing of the organic matter, an ozone generator may be employed to introduce ozone into the water upstream of the silver catalyst cartridge.

9 Claims, 8 Drawing Sheets

U.S. PATENT DOCUMENTS

| | | |
|---|---|---|
| 4,273,660 | 6/1981 | Beitzel .................................. 210/760 |
| 4,274,970 | 6/1981 | Beitzel .................................. 210/748 |
| 4,323,810 * | 4/1982 | Horstmann ............................. 313/24 |
| 4,422,450 * | 12/1983 | Rusteberg ........................... 128/62 A |
| 4,437,999 | 3/1984 | Mayne .................................. 210/748 |
| 4,694,179 | 9/1987 | Lew et al. ............................ 250/431 |
| 4,743,199 | 5/1988 | Weber et al. ......................... 433/216 |
| 4,752,401 | 6/1988 | Bodenstein ........................... 210/746 |
| 4,857,204 | 8/1989 | Joklik .................................... 210/695 |
| 4,892,712 | 1/1990 | Robertson et al. ................... 422/186 |
| 4,913,827 | 4/1990 | Nebel .................................... 210/748 |
| 4,968,437 | 11/1990 | Noll et al. ............................. 210/748 |
| 5,029,252 | 7/1991 | Ameseder .......................... 250/455.1 |
| 5,082,558 | 1/1992 | Burris ................................... 210/167 |
| 5,106,495 | 4/1992 | Hughes ................................. 210/139 |
| 5,106,501 | 4/1992 | Yang et al. ........................... 210/266 |
| 5,120,219 | 6/1992 | De Farcy ............................... 433/88 |
| 5,120,450 | 6/1992 | Stanley, Jr. ........................... 210/748 |
| 5,120,512 | 6/1992 | Masuda ................................. 422/297 |
| 5,141,636 | 8/1992 | Flanagan et al. ..................... 210/209 |
| 5,158,454 | 10/1992 | Viebahn et al. ........................ 433/82 |
| 5,178,755 | 1/1993 | LaCrosse ........................... 210/195.1 |
| 5,178,758 | 1/1993 | Hwang .................................. 210/256 |
| 5,180,499 | 1/1993 | Hinson et al. ........................ 210/706 |
| 5,207,993 | 5/1993 | Burris ................................... 422/256 |
| 5,213,773 | 5/1993 | Burris ................................... 422/256 |
| 5,266,215 | 11/1993 | Engelhard ............................. 210/748 |
| 5,268,104 | 12/1993 | Massoomain ......................... 210/638 |
| 5,302,298 | 4/1994 | Leitzke ................................. 210/748 |
| 5,352,369 * | 10/1994 | Heinig et al. ......................... 210/760 |
| 5,393,490 | 2/1995 | Jacob ...................................... 422/22 |
| 5,431,861 * | 7/1995 | Nagahiro ........................... 261/140.1 |
| 5,520,893 | 5/1996 | Kasting, Jr. .......................... 422/305 |
| 5,540,848 | 7/1996 | Engelhard ............................. 210/748 |
| 5,547,590 | 8/1996 | Szabo ................................... 210/748 |
| 5,709,799 * | 1/1998 | Engelhard ............................. 210/748 |
| 5,935,431 * | 8/1999 | Korin .................................... 210/205 |
| 5,942,125 * | 8/1999 | Engelhard et al. ................... 210/748 |

OTHER PUBLICATIONS

"Microbial Contamination of Dental Unit Waterlines: Prevalence, Intensity and Microbiological Characteristics", by J. Williams et al., *Journal of the American Dental Association*, vol. 124, Oct. 1993, pp. 59–65.

"Detecting Legionella Pneumophila in Water Systems: A Comparison of Various Dental Units", by S.J. Challacombe et al., *Journal of the American Dental Association*, vol. 126, May 1995, pp. 603–608.

"Safe Water in the Dentist's Office", by G. Shaparenko, *Water Conditioning & Purification*, Jun. 1995, pp. 60 and 62–65.

Article: *The Catalyst Review Newsletter*, entitled "Fountainhead Technologies Talks About Their Unique Approach to Catalytic Water Purification", Nov. 1994 (4 pages).

"Material Safety Data Sheet", prepared by Fountainhead Technologies, Inc., Providence, RI (4 pages).

* cited by examiner

Office#1

| DATE SAMPLED | HANDPIECE(A) | AIR/WATER 1 |
|---|---|---|
| 8/14/98 - Before | 220,000 | 450 |
| 8/14/98 - After | 1 | 1 |
| 8/21/98 | 3 | 4 |
| 8/28/98 | 0 | 0 |

Office#2

| DATE SAMPLED | HANDPIECE(A) | AIR/WATER 1 |
|---|---|---|
| 8/7/98 - Before | 34,000 | 355,000 |
| 8/13/98 -After (samples from 8/7/98) | <100 | 0 |
| 8/12/98 | 0 | 0 |
| 8/20/98 | 0 | 0 |
| 8/27/98 | 0 | 0 |

Office#3

| DATE SAMPLED | HANDPIECE(A) | AIR/WATER 1 |
|---|---|---|
| 8/14/98 - Before | 9,400 | 12,150 |
| 8/14/98 - After | 80 | 13 |
| 8/21/98 - | 5 | 23 |

Office#4

| DATE SAMPLED | HANDPIECE(A) | AIR/WATER(A) |
|---|---|---|
| 8/7/98 -Before | 40,000 | 41,000 |
| 8/7/98 -After | 0 | 0 |
| 8/13/98 | 0 | 0 |
| 8/20/98 | 0 | 0 |
| 8/27/98 | 0 | 0 |

Office#5

| DATE SAMPLED | HANDPIECE(A) | AIR/WATER(A) |
|---|---|---|
| 8/7/98 - Before | 212,000 | 89,500 |
| 8/7/98 - After | 0 | 0 |
| 8/13/98 | 0 | 0 |
| 8/19/98 | 0 | 1 |
| 8/28/98 | 0 | 0 |
| 9/2/98 | 0 | 0 |

Office#6

| DATE SAMPLED | HANDPIECE(A) | AIR/WATER(A) |
|---|---|---|
| 8/25/98 - Before | 4,100 | 350 |
| 8/25/98 - After | 0 | 0 |
| 9/4/98 | 0 | 0 |

FIG. 11

CATALYTIC DENTAL WATER APPARATUS

CROSS-REFERENCE RELATED APPLICATIONS

This application is a continuation-in-part application of U.S. application entitled "Dental Unit Water Purifier", assigned Ser. No. 08/648,204, filed May 14, 1996, now U.S. Pat. No. 5,942,125, issued on Aug. 24, 1999. The present application claims priority to a provisional application entitled "Catalytic Dental Water Apparatus", assigned Ser. No. 60/089,541, filed Jun. 17, 1998, both of which applications describe inventions by the present inventors.

BACKGROUND OF THE INVENTION

1. Field of the Invention

The present invention relates to purification of dental water lines, to destroying biofilm that may be present and to preventing biofilm buildup and, more particularly, to having oxygen or ozone enriched water react with a silver catalyst and oxidize organic matter, such as microorganisms and biofilm, that may be present in the water, on surfaces of the dental water lines and on the surfaces of any downstream handpieces, implements or nozzles, to provide uncontaminated water at the point of use.

2. Description of Related Art

Tap water in dental offices is similar to tap water in most homes and offices. While this water is generally considered safe to drink, it is never sterile. Most tap water samples contain fewer than 50 cfu (colony forming units) of bacteria per milliliter (cfu/ml). However, once the water leaves plumbing lines and enters the long plastic tubing that feeds into dental high-speed handpieces and other dental implements, such as air-water syringes and ultrasonic tooth scalers, the environment changes. Here, the flow rate, frequent periods of stagnation and large relative surface area of the small bore plastic lines are ideal for microbial contamination.

Water that stagnates in plastic water lines and/or tubing overnight and even during long periods during the day provide bacteria the opportunity to stick to the wall of the lines/tubing. Water, slowly running through the line, provides a constant flow of bacteria that can adhere to the microbes that are already clinging to the wall. A cooperating population of several different species, which depend on each other for survival or are otherwise symbiotically related, continue to multiply and form a matrix that provides nutrients and mutual protection.

This bacterial population is known as biofilm, a microbial mass that is bathed in liquids. Dental plaque is another example of biofilm. Biofilm can also be found in air conditioning units, artificial implants and many types of equipment, including dental anti-siphon and check valves.

The function of the anti-siphon and check valves is to prevent aspiration of patients' fluids into the dental water lines. Unfortunately, these valves often fail to work properly because of biofilm and other factors.

Microbes can become drawn back into the dental water lines as a result of imperfect hygiene sterilization practices, a transient negative pressure when the drill stops rotating and/or mechanical failure of anti-siphon valves or other mechanisms. Once this happens, pathogens originating from patients' mouths can enter the lines and adhere to existing biofilm and multiply within them.

These microbes, originating both upstream from municipal water supplies and downstream from patients' blood and saliva, are not very numerous initially. Amplification of the microorganisms is nothing less than astounding. Microbial studies of dental water lines reveal bacterial population explosions averaging over 500,000 cfu/ml and often exceeding 1,000,000 cfu/ml.

Thus far, researchers have identified pathogens and opportunists in dental equipment such as Pseudomonas, Legionella, Staphylococci, Streptococci, Nocardia, Serratia, Klebsiella, Moraxella, Bacteroides, Flavobacterium, Escherichia, several species of amoebae known to serve as hosts for *Legionella pneumophila* and even nematodes (worms).

Various solutions to prevent exposure of dental patients to contaminated water have been proposed. Such proposals include flushing the dental water lines with distilled water or chemicals but little evidence exists that such flushing eliminates the biofilm. Sterilization of dental instruments between patients has little effect in preventing the microbes in the dental water from entering the next patient's mouth. Using new disposable sterile water lines between patients does not solve the problem of biofilm upstream of the replaced lines and the costs are significant. Use of containers having sterile or distilled water is effective only if the water conveying lines are replaced after each patient and if the water does not become contaminated prior to disposal of used water lines. Use of check valves to prevent backflow is essentially ineffective one hundred percent (100%) of the time due to contamination of the valve itself. Use of electrical current in combination with antimicrobial agents is impractical due to unavailability of inexpensive ready-to-use equipment. Distilling the water received from a municipal water source only addresses the water and not the contaminants present in the lines conveying the water to the patient. To date, devices using 0.2 micron filters or the like are reasonably effective to prevent transmission therepast of microbes provided that the filters are replaced at least daily and that the process of such replacement does not permit a colony of microbes to be conveyed to a water line downstream of the filter. It is therefore evident that a significant health hazard exists for patients within a dental office and no viable solution is presently commercially available.

SUMMARY OF THE INVENTION

In the present invention, oxygen, whether from ambient air or a source of oxygen, or ozone from an ozone generator, is introduced to a water source through a sparger or the like to entrain the oxygen or ozone in the water. The water is subsequently conveyed past a silver catalyst cartridge through water lines to each of the various handpieces or water flow dependent implements used by a dentist during the normal course of providing dental services. The oxygen entrained in the water is attracted to the silver in the cartridge and will dissociate from its normal diatomic state to bond with the silver. However, this bond is weak enough that the oxygen will dissociate to oxidize organic matter, including microorganisms in the water. A small amount of the silver will dissolve in the water stream flowing therepast and flow downstream. A portion of this silver will adhere to the surfaces of the water lines, handpieces and implements. The adhered silver is free to react with the oxygen dissolved in the water and any attendant biofilm will be destroyed. Any ozone introduced into the water will destroy any microbial pathogens in the water and help render the water essentially microbe free. Furthermore, the living organisms in any biofilm attendant the walls of the water lines, handpieces and implements will be destroyed upon contact with the ozone. Thus, the water delivered to a patient's oral cavity during the rendering of dental services will be essentially free of any viable microbial activity.

It is therefore a primary object of the present invention to provide apparatus for delivering water from dental water lines free of any living microbes.

Another object of the present invention is to provide apparatus for destroying any biofilms formed on the walls of water lines, handpieces and nozzles in a dental operatory.

Yet another object of the present invention is to provide apparatus that delivers to a dental patient water free of microbial activity whether such water be from a municipal water system or a water container.

Still another object of the present invention is to provide apparatus for destroying any microorganisms present in dental water line or the water itself whether the water is flowing through the line or is stagnant.

A further object of the present invention is to provide a silver catalyst to enhance oxidization of microorganisms and biofilm attendant dental handpieces and other dental implements.

A yet further object of the present invention is to provide inexpensive apparatus for ensuring that water delivered to a dental patient is free of living microbes.

A still further object of the present invention is to provide a method for inexpensively and effectively destroying any biofilm and preventing biofilm buildup attendant dental water lines, dental handpieces and related implements.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 8 illustrates apparatus for entraining air or oxygen in water and passing the mixture through a silver catalyst cartridge;

DETAILED DESCRIPTION OF THE PREFERRED EMBODIMENT

Figure 1:
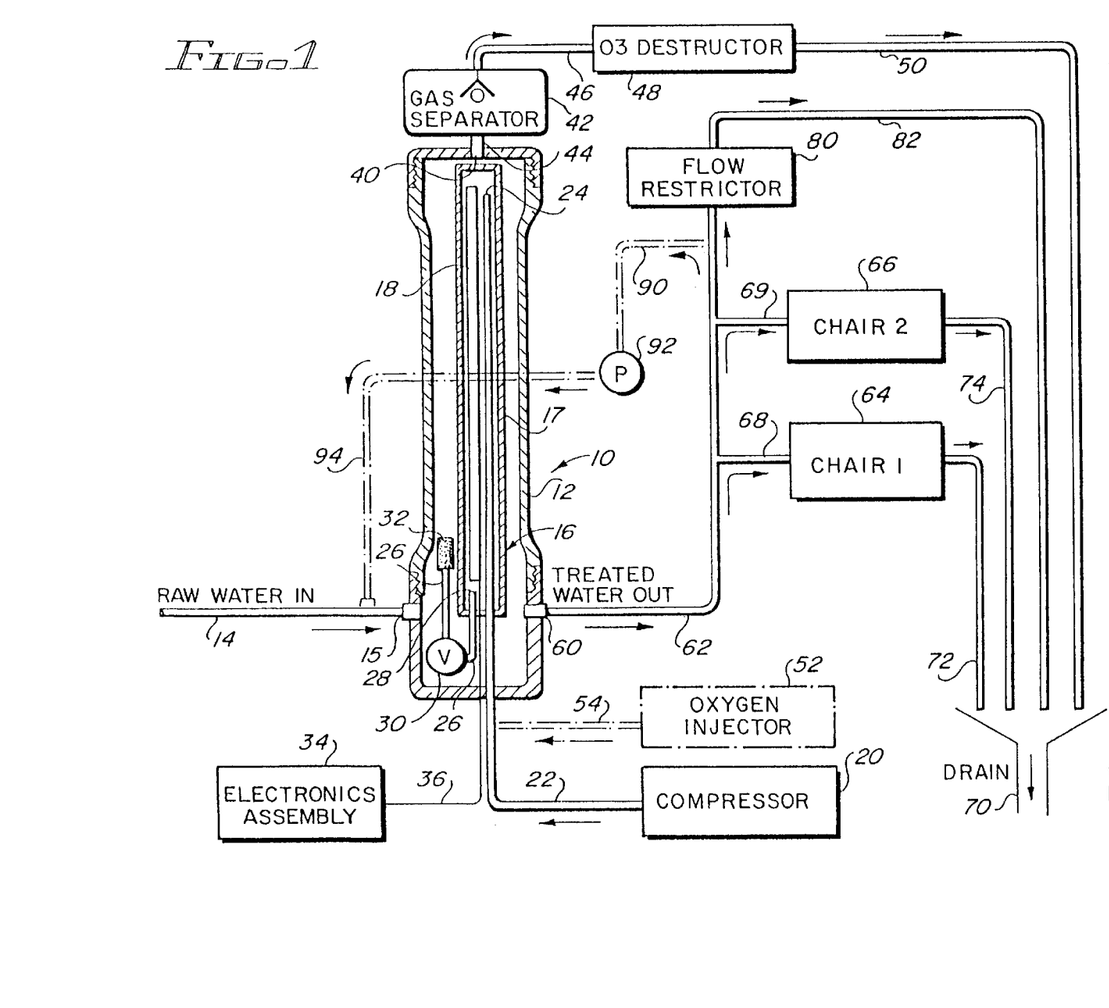
FIG. 1 illustrates apparatus for ozonating water delivered to a dental chair.

Ozone entrained in water will destroy microbial life forms in the water itself as well as in any biofilm on the containers for the water or upon the walls of channels or lines through which the ozonated water flows because ozone is a viricide, bactericide, and algicide. Referring to FIG. 1, there is shown apparatus 10 for ozonating water entering a dental office to provide ozonated water to each dental chair. The ozonated water will destroy any microbes or pathogens within the water and reduce or terminate the motility and viability of microbial activity in any biofilm that may be present on the walls of the water lines and attendant dental implements. Furthermore, the ozonated water will terminate the motility and viability of any microbes or pathogens aspirated from a patient and entering any water channels in the dental implements and the water lines extending from the dental implements.

Figure 2:
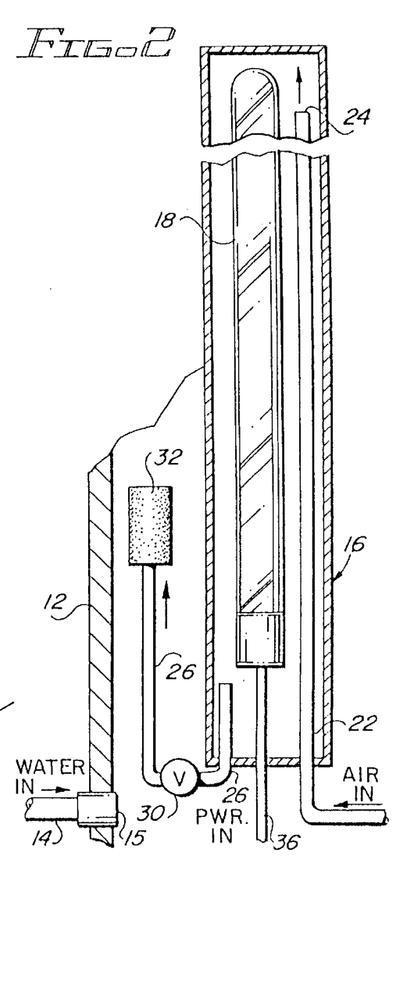
FIG. 2 illustrates details of the ozonating apparatus shown in FIG. 1.

With joint reference to FIGS. 1 and 2, apparatus 10 includes a container 12 for receiving water from a water line 14. An ozone generator 16 is disposed within container 12 and includes a lamp or tube 18 for emitting ultraviolet light within a watertight steel cylinder 17. A compressor 20 provides a source of air under pressure through pipe 22 into ozone generator 16. Outlet 24 of pipe 22 may be at the upper end of the ozone generator, as illustrated. A pipe 26 extends from within the ozone generator and includes an inlet 28 located at the lower end of ozone generator 16. Thereby, air flowing into the generator through outlet 24 is forced to pass around and along tube 18 to inlet 28 to increase the exposure of the air to the ultraviolet radiation from the tube. It is well known that the oxygen in the air subjected to ultraviolet light will result in conversion of the oxygen molecules into ozone molecules as a function of the intensity of and exposure time to ultraviolet radiation. Thus, ozone enriched air flows into pipe 26 through inlet 28. A check valve 30 in pipe 26 prevents reverse flow therethrough. Pipe 26 is terminated by a sparger 32. The sparger emits the ozone enriched air in the form of tiny bubbles which become readily entrained and/or dissolved in the water in and flowing through container 12.

An electronics assembly 34, connected to a suitable power source, provides the requisite electrical power through conductor 36 to tube 18 to bring about energization of the tube and emission of ultraviolet radiation. To prevent an accumulation of ozone enriched air within container 12, any such gaseous compound is evacuated through an outlet 40 leading to a gas separator 42 through a pipe 44. Outflow from the gas separator is through a pipe 46 to an ozone destructor 48. The remaining air is discharged through a pipe 50 to a drain or the like to accommodate drainage of any moisture that may accumulate downstream of container 12.

As an alternative to air injection, oxygen may be injected into ozone generator 16 to provide a higher concentration of ozone in the gas discharged from sparger 32. A source of oxygen and an injector for propelling oxygen into the ozone generator is represented by numeral 52 identifying an oxygen injector. The oxygen is injected through pipe 54 into the ozone generator. It is to be understood that injection of air or oxygen is primarily in the alternative although oxygen enriched air could also be injected.

The ozonated water produced within container 12 is discharged through outlet 60 into conduit 62. The conduit serves as a water line to provide ozonated water at each of chairs 64,66, etc. in a dental office. In particular, branch lines 68,69 may extend from conduit 62 to a manifold or the like attendant each dental chair and in fluid communication with dental implements and other devices that normally discharge the water received. Waste water generated at chair 64 is conveyed to a drain 70 through drain line 72. Similarly, waste water generated at chair 66 is conveyed to drain 70 through drain line 74. Such drain lines would be present for each chair.

Ozone entrained in water is somewhat unstable and will revert to the molecular form of oxygen at a higher or lower rate depending upon a number of variables. To ensure a fresh supply of ozonated water within conduit 62 after periods of inactivity or non-flow of ozonated water through one or more of branches 68,69, a flow restrictor 80 may be employed. Such flow restrictor accommodates a low flow rate of ozonated water continuously through conduit 62 into discharge pipe 82 and drain 70. Alternatively, a return line 90 is in fluid communication with conduit 62 downstream of the last branch leading to a dental chair. Ozonated water from conduit 62 is drawn into the return line by a pump 92. The pump conveys the ozonated water through return line 94 into water line 14 upstream of inlet 15 in container 12. Thus, the ozonated water flowing through the return line, which water may have a lowered concentration of entrained ozone, is reintroduced to the ozone generator. Such reintroduction, rather than simply having the ozonated water recirculate through conduit 62 and the return line, ensures that water having at least a minimum level of entrained ozone is always present at each of the branch lines (such as branch lines 68,69).

Figure 3:
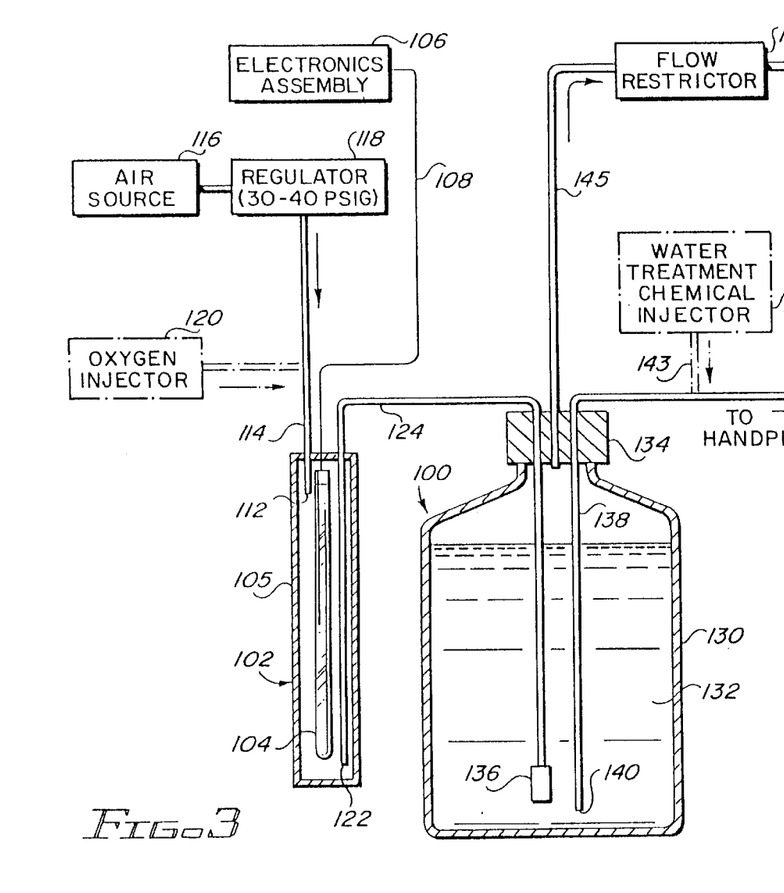
FIG. 3 illustrates apparatus for ozonating water within and delivered from a water container to a dental chair.

For reasons set forth above, a number of dental offices have begun to use bottles of distilled or purified water instead of relying upon the municipal water system to satisfy the water needs. Referring to FIG. 3, there is illustrated a variant apparatus 100 for use in conjunction with such bottled water. An ozone generator 102 includes a lamp or tube 104 disposed within a closed steel cylinder 105 and connected to an electronics assembly 106 through a conductor 108. Upon energizing the electronics assembly, electrical power is provided to tube 104 causing it to emit ultraviolet radiation. The air within cylinder 105 of ozone generator 102 will be irradiated to cause a molecular change of the oxygen into ozone. An inflow of air is provided from outlet 112 of pipe 114 connected to an air source 116 under pressure. A regulator 118 may be disposed in pipe 114 to regulate the pressure of the air flowing into the ozone generator. As suggested by the dashed box identified as an oxygen injector 120, oxygen may be discharged through outlet 112 into cylinder 105 or a mixture of air and oxygen may be discharged into the cylinder. The ozone enriched air within cylinder 105 flows out through inlet 122 of pipe 124. As illustrated, outlet 112 and inlet 122 are at opposite ends of tube 104 to maximize exposure of the air to the ultraviolet radiation emitted from tube 104 and thereby enhance the ozone enriched air.

Bottle 130 containing distilled or otherwise purified water 132 includes a stopper 134 for sealing the bottle against contact between the ambient air and water 132. Pipe 124 extends through stopper 134, illustrated, and is terminated by a sparger 136 located in proximity to the bottom of bottle 130. The purpose of the sparger is that of discharging the ozone enriched air into the water in the form of tiny bubbles to enhance entrainment within the water. A discharge conduit 138 includes an inlet 140 proximate the bottom of bottle 130. The ozone enriched water (ozonated water) within bottle 130 is conveyed via discharge conduit 138 through stopper 134 to the various dental handpieces or other water related dental implements. Thereby, these handpieces and implements are supplied with ozonated water which will have the effect of destroying the motility and killing any bacteria, microbes or microorganisms present in either the water or in any biofilm on the wall of the discharge conduit or the walls of channels in the handpieces or dental implements. Under certain circumstances, it may be beneficial to treat chemically the water flowing to the dental handpieces and other implements. This may be accomplished by incorporating a chemical injector 142 in fluid communication via conduit 143 with discharge conduit 138 downstream of bottle 130.

A certain amount of ozone enriched air will separate from water 132 and collect at the top of bottle 130. This ozone is discharged through discharge line 145 extending through stopper 134 from within the bottle. The impetus for such discharge results from the pressure within the bottle generated by the inflowing ozone enriched air through sparger 136. The rate of ozone discharge through line 145 is controlled by flow restrictor 146. To prevent damage to the ambient environment, an ozone destructor 147 eliminates the ozone molecules such that the resulting venting through outlet 148 is a gas essentially ozone free.

Figure 4:
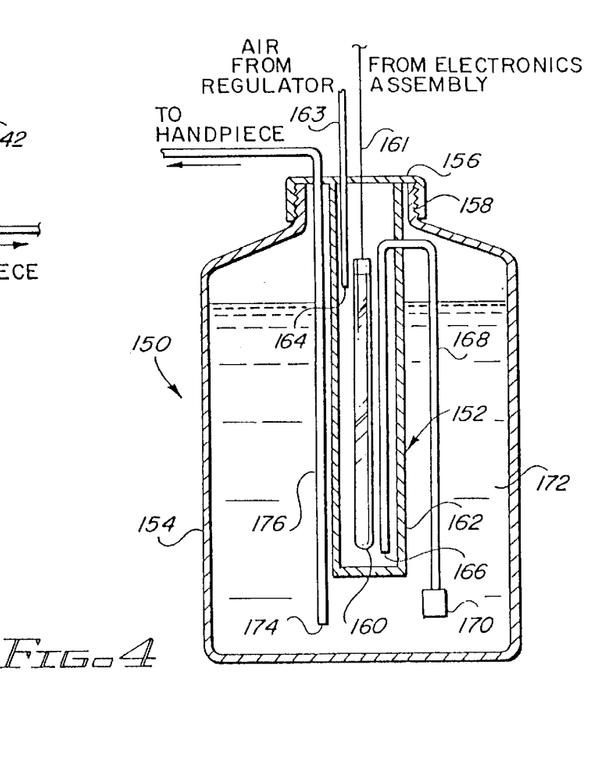
FIG. 4 illustrates apparatus contained within a water container for delivering ozonated water from the container to a dental chair.

Referring to FIG. 4, there is illustrated a further variant apparatus 150 similar to variant apparatus 100 shown in FIG. 3 except that ozone generator 152 is disposed within bottle 154. The ozone generator may be suspended from or otherwise attached to cap 156 in threaded engagement with neck 158 of bottle 154. A lamp or tube 160 for emitting ultraviolet radiation is disposed within a closed steel cylinder 162 of ozone generator 152. It is electrically connected to an electronics assembly via a conductor 161. Air, oxygen, or a mixture of air and oxygen is pumped into the ozone generator through a pipe 163 having an outlet 164 proximate one end of tube 160. The ozone enriched air produced by radiation from tube 160 is discharged into inlet 166 of pipe 168. The pipe, which may extend through a wall of cylinder 162, as illustrated, discharges the ozone enriched air through a sparger 170 located in proximity to the bottom of bottle 154 to enhance entrainment of the ozone enriched air in water 172 as the minute bubbles from the sparger migrate upwardly. The ozone enriched water or ozonated water is discharged from within bottle 154 through inlet 174 of conduit 176. As indicated, conduit 176 conveys the ozonated water to the dental handpieces and other dental implements using water as part of their function. As noted in the drawing, the air flow from outlet 164 to inlet 166 within cylinder 162 is essentially along the full length of tube 160 to enhance exposure of the air to ultraviolet radiation and thereby promote transformation of the oxygen molecules into ozone molecules.

Figure 5:
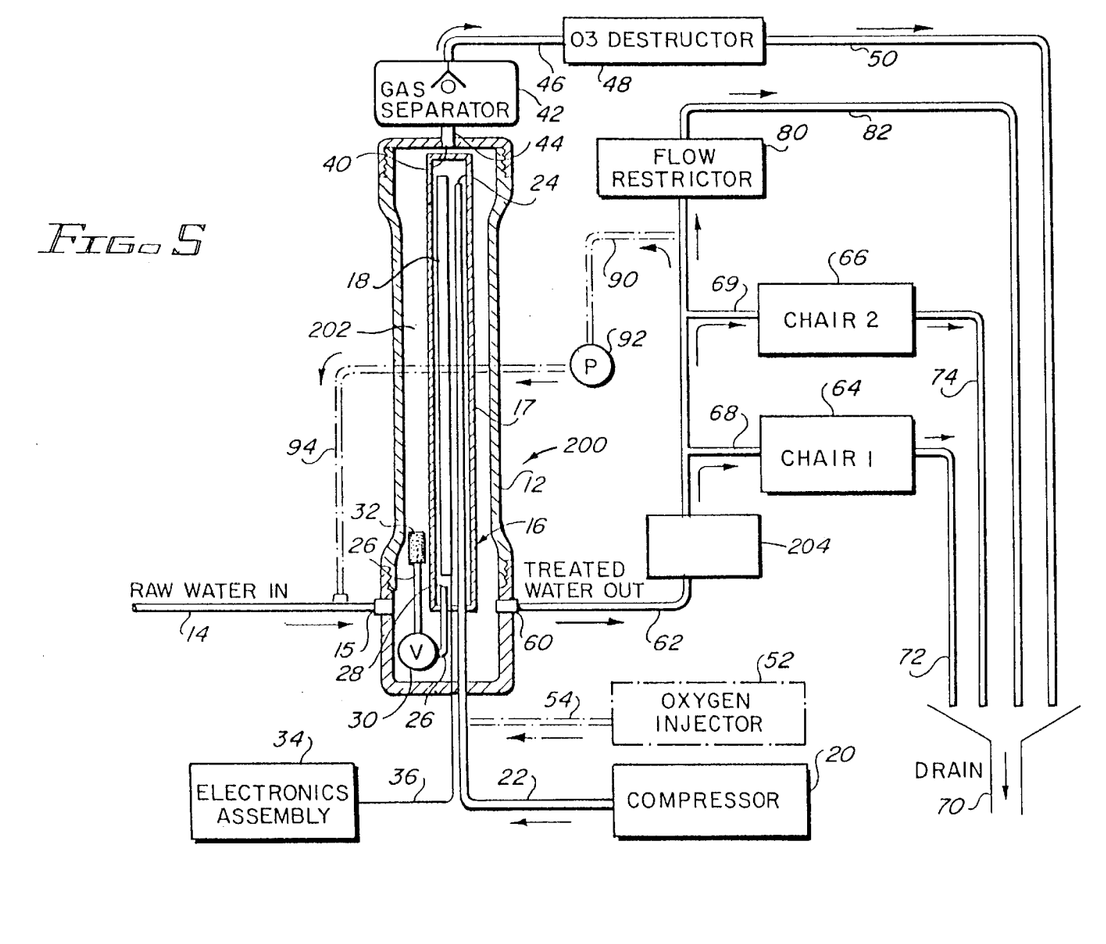
FIG. 5 illustrates the apparatus shown in FIG. 1 with the addition of a silver catalyst cartridge.

Referring to FIG. 5 there is shown an apparatus 200 similar to a great extent with apparatus 10 shown in FIG. 1. For identification purposes, the same reference numerals for common elements will be used. By operation of ozone generator 16, a combination of air and ozone is introduced into water 202 within container 12 by sparger 32. Accordingly, the water outflowing from container 12 through conduit 62 will have a mixture of entrained and/or dissolved oxygen and ozone. Prior to flow of this mixture into branch lines 68,69 etc. It is passed through a silver catalyst cartridge 204. Within the cartridge, the oxygen entrained/dissolved in the water makes contact with the silver and will dissociate from its normal diatomic state to bond with the silver. However, this bond is weak enough that the oxygen will dissociate to oxidize organic matter (such as microorganisms) in contact therewith. Through such oxidation, the microorganisms, which are the major dangerous constituents of biofilm and present potential health hazards, will be destroyed. Thereby colonization of such microorganisms will not and cannot occur. Additionally, a small amount of silver dissolves into the water flowing therepast and conveyed downstream through branch lines 68,69, etc. to the various handpieces and dental implements attendant each of chairs 64,66 etc. A portion of the silver dissolved into the water will adhere to the interior surfaces of the branch lines, the handpieces and the implements. Upon such adherence, the silver is free to react with the oxygen conveyed therepast by the flowing water. Typically, the concentration of silver is only order of about three parts per million (3 mg/L).

The apparatus shown in FIG. 5 provides numerous beneficial features for a dental operatory or other medical facility using water from a municipal water source. The introduction of ozone into the water has the beneficial effect of sterilizing the water received. By using a sparger, to introduce the ozone and attendant air from the ozone generator establishes elevated levels of oxygen and ozone in the water. The solubility of the ozone in the water is essentially proportional to the pressure. The ozone assists in biofilm reduction by dissociating to form oxygen containing radicals which will react (oxidize) organic matter and microorganisms. Additionally, the presence of ozone within the silver catalyst cartridge increases the activity of the silver catalyst and thereby increases the reaction rate between the silver and oxygen. It is believed that an interaction between the silver and the ozone may cause some reaction with the water itself to convert a small amount of the water to hydrogen peroxide; it is well known that hydrogen peroxide is a strong oxidizer and functions as a disinfecting agent. Accordingly, the presence of hydrogen peroxide may have a further beneficial effect in destroying existing biofilm and preventing the formation of biofilm. As the ozone is carried downstream, it will spontaneously decompose to oxygen and its effectiveness for biofilm destruction will be reduced. However, the silver present in the water and adhered to the walls of the conduits, pipes, handpieces and implements will react with the dissolved oxygen decomposed from the ozone and provide further destruction of organic matter and the microorganisms. As a result of the combination of ozone and oxygen entrainment in the water and the silver catalyst, the water flowing into the dental handpieces and dental implements will be sterile and a residual disinfecting agent will exist throughout the plumbing network of a dental operatory.

For the above and below described configurations employing ozone, it may be prudent from time to time to purge the water conduits and related water conveying equipment with ozone. Such purging, after evacuation of all water, would expose and tend to destroy any residual biofilm that may be present on the exposed surfaces.

The use of ozonated water, with or without purging with ozone, will help keep the water conduits and associated equipment clean. Thus, the maintenance (cleaning) is reduced and the performance and life of dental drills, irrigation faucets and all water using dental tools will be enhanced.

Figure 6:
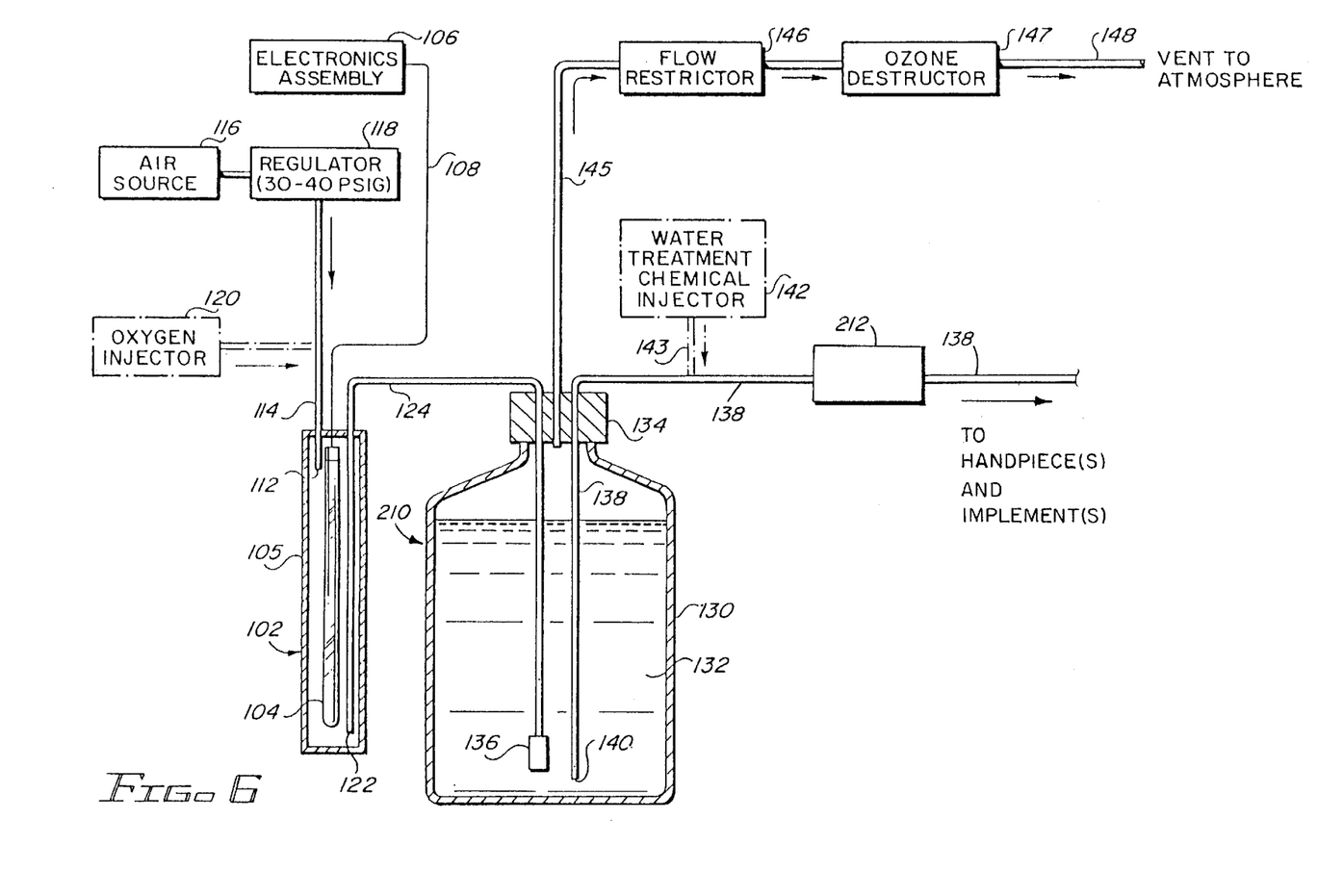
FIG. 6 illustrates the apparatus shown in FIG. 3 with the addition of a silver catalyst cartridge.

Referring to FIG. 6 there is shown an apparatus 210, which apparatus is similar to that shown in FIG. 3. With respect to common elements, the same reference numerals will be applied. The major difference between the apparatus 100 (FIG. 3) and apparatus 210 is the introduction of a silver catalyst cartridge 212 in series with discharge conduit 138. As set forth in further detail with reference to FIG. 3, sparger 136 introduces ozone and oxygen to water 122 with container 130. The ozone and oxygen is entrained and to some extent dissolved in the water overflow through discharge conduit 138 and enters silver catalyst cartridge 212. The beneficial effects of the water outflowing from the cartridge through discharge conduit 138 will be essentially the same as discussed above with respect to FIG. 5.

Figure 7:
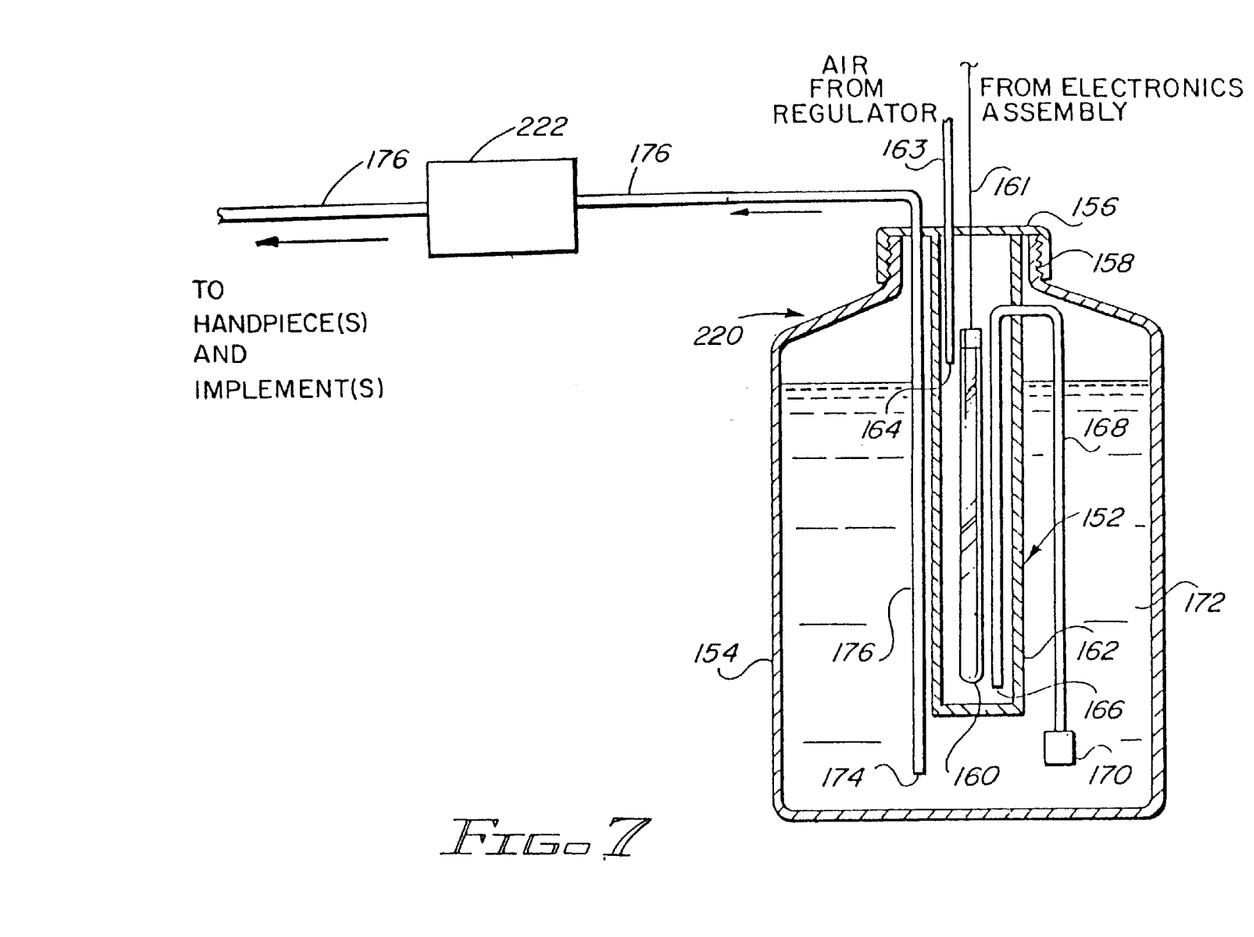
FIG. 7 illustrates the apparatus shown in FIG. 4 with the addition of a silver catalyst cartridge.

FIG. 7 illustrates apparatus 220, which is essentially the same as apparatus 150 shown in FIG. 4. Accordingly, common elements have been given the same reference numerals. Apparatus 220 includes a silver catalyst cartridge 222 disposed in series in conduit 176 conveying water to the various handpieces and implements, as discussed above. The ozone and oxygen discharged by sparger 170 into water 172 contained in container 154 is transmitted to and through silver catalyst cartridge 222. The reactions within the cartridge and beneficial effects of the water flowing therefrom discussed above with respect to FIGS. 5 and 6 will also be true for the water flowing from cartridge 222 of apparatus 220.

FIG. 8 illustrates an apparatus 230 similar in many respects to the apparatus shown in each of FIGS. 5, 6 and 7 except that an ozone generator is not formed a part thereof. The deletion of the ozone generator constitutes a significant cost reduction and avoids maintenance efforts and expenses associated therewith. Apparatus 230 includes a container 232, which may be referred to a saturation chamber (a term which could also be applied to the containers associated with each of apparatus 200, 210 and 220). A source 234 of air, which could be air from a dental operatory supply, is conveyed through a conduit 236 into container 232. A regulator 238 may be disposed in conduit 236 to maintain the pressure therein at a predetermined pressure, such as 45 psig. To prevent overflow from container 232 through conduit 236 a check valve 230 may be employed in the conduit. A sparger 242 is disposed at the terminal end of conduit 236 to introduce fine bubbles of air into water 244 to entrain/dissolve these bubbles in the water. To prevent a buildup of an air space 246 within container 232, a vent conduit 248 may be employed. Such conduit would include a flow restrictor 250 to prevent discharge of water therethrough. The air (gas) flow past the restrictor may be vented to the atmosphere through an outlet 252.

To increase the amount of oxygen to be entrained in water 244, a source 254 of oxygen may be employed, as depicted in dashed lines. The oxygen is conveyed through conduit 256 from the source of oxygen into conduit 236. A valve 258 may be used to select inflow from either source 234 of air or source 254 of oxygen; alternatively, a valve capable of metering a flow from each of the sources of air and oxygen may be used.

Because each of the source of air and the source of oxygen must be under pressure to cause gas to flow therefrom into conduit 236, water 244 in container 232 becomes pressurized. Such pressure environment also assists in expelling gas through vent conduit 248 to prevent existence of a significant air space 246. The pressure environment present within container 232 causes the water to be discharged into inlet 260 of discharge conduit 262. The discharge conduit conveys the water with entrained air/oxygen to silver catalyst cartridge 264. The chemical reactions resulting within the cartridge are the same as those described above with respect to FIGS. 5, 6 and 7. The outflow from the cartridge is conveyed via conduit 266 to the branch lines associated with each dental chair and the related handpieces and implements, as described above. To further assist in destroying microorganisms within the water discharged from container 232, a UV source 268 may be used in conjunction with discharge conduit 262 to irradiate the water flowing therepast and thereby kill irradiated microorganisms. As UV source 268 is an alternate embodiment, it is shown in dashed lines.

Referring jointly to FIGS. 9, 10a, 10b and 10c, a representative silver catalyst cartridge will be described in detail. A cartridge of this type may be used as each of the silver catalyst cartridges discussed above. The cartridge is formed of a tube or sleeve 282 having an interior diameter of 0.0875 inches and of a 2 inch length. A plug 284 is disposed at each end. The plug includes a cylinder 286 for insertion into an end of sleeve 282 and an annular protrusion 288 to limit insertion of the plug. A centrally located threaded aperture 290 is formed in the plug to threadedly receive a fitting 292 having a barbed nipple 294 extending therefrom for penetrable engagement with an attached conduit. A downstream fitting engaging downstream plug 284 may be similar to fitting 292; alternatively, it may be a fitting 296 threaded engaging plug 284 and configured to receive and engage the end of tubing or a conduit extending therefrom. A twenty micron (20 $\mu$) filter 298 may be attached to the downstream plug, which filter prevents outflow of particulate material larger than twenty microns. Silver catalyst 298 comprises beads of silver packed between the end plugs within sleeve 282. These beads comprise silver deposited on a mineral substrate (alumina) and are available from Fountainhead Technologies, Inc. of Providence, R.I. They are described in further detail in an article entitled "Fountainhead Technologies talks about their unique approach to catalytical water purification" published in the November, 1994 issue of the Catalyst Review Newsletter, which article is incorporated herein by reference. As set forth in a Material Safety Data Sheet prepared by Fountainhead Technologies, Inc. and incorporated herein by reference, the ratio of alumina ($Al_2O_3$) to silver (Ag) is in the range of about 97.9% to about 98.3% and in the range of about 2.1% to about 1.7%, respectively.

Figure 9:
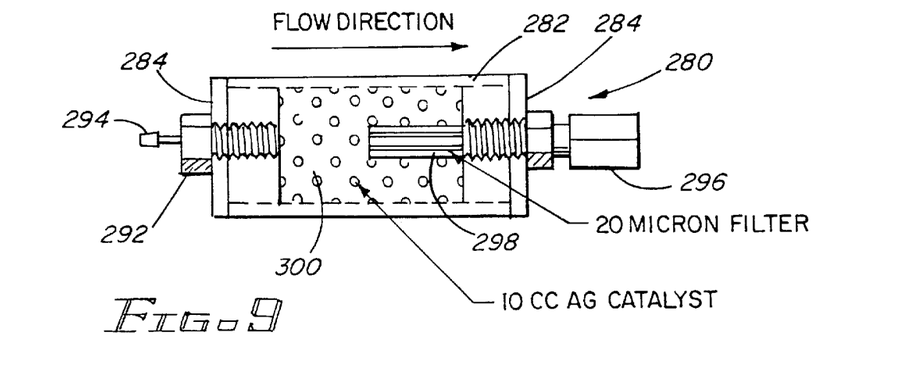
FIG. 9 illustrates a silver catalyst cartridge.
Figure 10A:
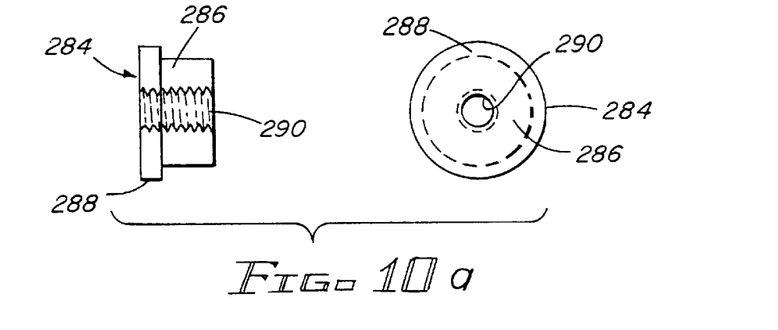
FIGS. 10a, 10b, and 10c illustrate components of the cartridge shown in FIG. 9.
Figure 10B:
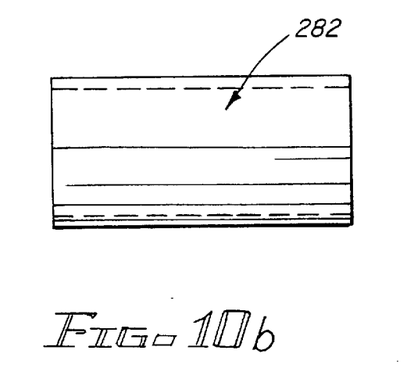
Figure 10C:
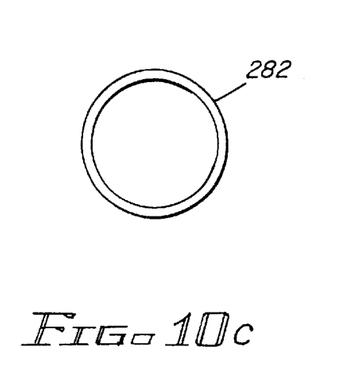

As described above, the silver catalyst cartridge works essentially in the following manner. Dissolved oxygen in the water flowing through the cartridge contacts the beads of silver. The bond of diatomic oxygen molecule is ruptured upon contact to create individual oxygen atoms which then become loosely bound to the silver surface. The unique ability of silver to enter into oxidative reactions is due to the very weak bond it forms with oxygen (approximately 7 to 8 kcal/mol; most other transition metals bond with oxygen at strengths of more than 100 kcal/mol). These weak bonds allow silver to readily transfer the loosely held oxygen atoms to any oxidizable substrate, such as organic matter and microorganisms. When other organic matter and microorganisms make contact with the loosely bound oxygen atoms, oxidation occurs and the bonds in the organic matter and microorganisms are ruptured. The oxidized fragments will depart from the surface of the silver beads to expose the beads and the process is repeated. Silver ions are slowly released into the water by a combination of erosion and galvanic action. The silver ions so produced provide a residual oxidation activity downstream to affect any organic matter or microorganisms coming in to contact therewith.

Figure 11:
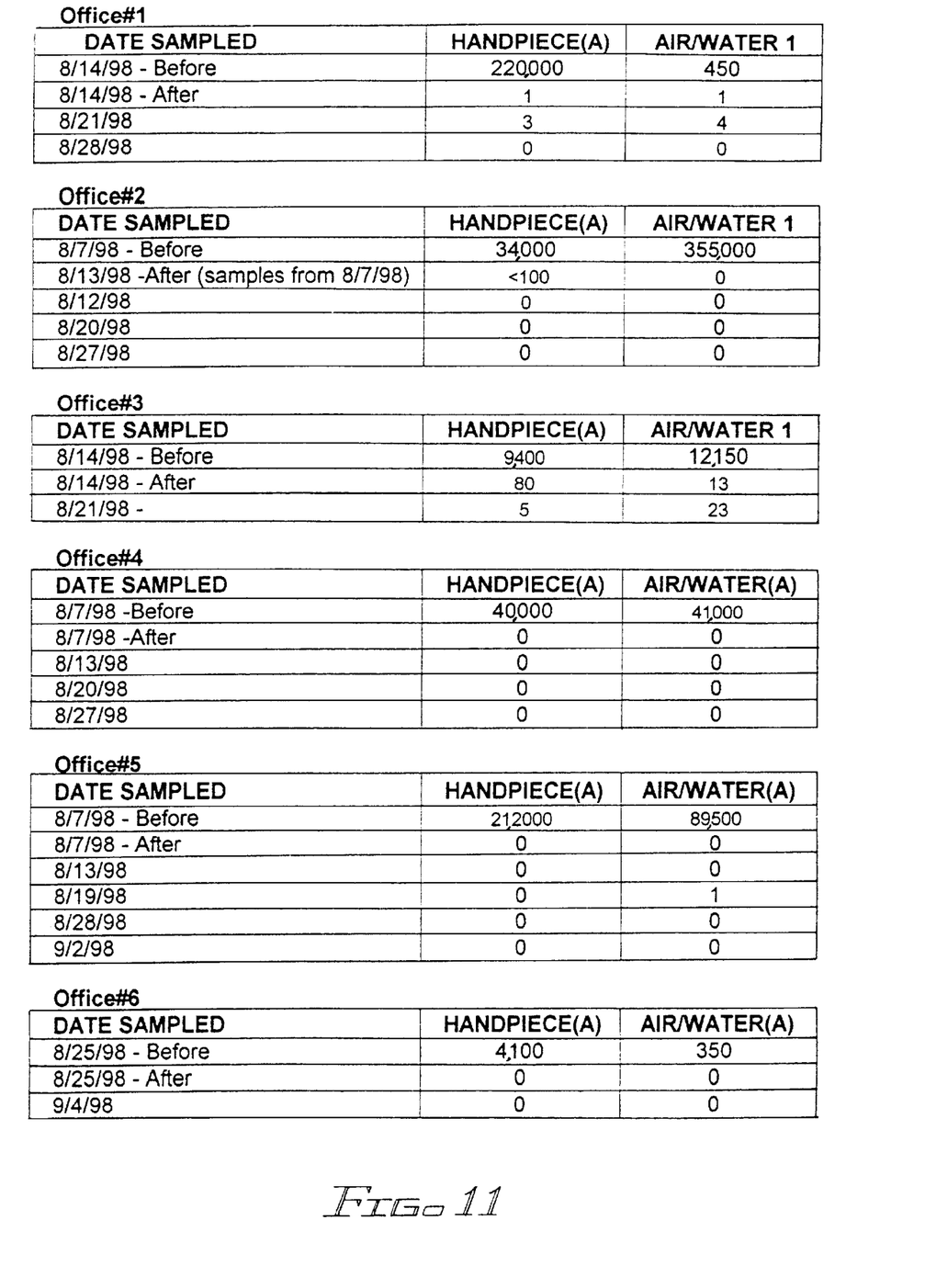
FIG. 11 illustrates test results obtained with the present invention.

To test the efficacy of the present invention, a number of experiments were conducted in different dental office locations. The results of these experiments are tabulated in FIG. 11. During these tests, the number of colony forming units (cfu) per millimeter at each noted sampling cite were recorded. In office No. 1 prior to use of the present invention, the water at handpiece A had 220,000 cfus and a water irrigation implement had 450 cfus. During the succeeding three weeks, the number of cfus dropped to 1,3 and 0 and 1,4, and 0, respectively. In office No. 2, a handpiece A and a water irrigation implement prior to installation of the invention had 34,000 cfus and 355,000 cfus, respectively. After one week, the sample at handpiece A contained less than 100 cfus and there were none in the irrigation implement. For the following three weeks, there were no cfus measured at either the handpiece A or the irrigation implement. In the office No. 3, prior to use of the invention, handpiece A had 9,400 cfus and water irrigation implement had 12,150 cfus. After installation of the invention, the cfus at handpiece A dropped to 80 and the cfus at the irrigation implement dropped to 13. After a week, the cfus at handpiece A dropped to 5 and cfus at the irrigation implement increased to 23 (the reason for the increase is unknown and may have been poor data or due to an intervening activity). In office No. 4, the number of cfus at handpiece A was 40,000 and at water irrigation implement was 41,000 prior to installation of the invention. Thereafter, the cfus dropped to zero after installation and for the ensuing four weeks. In office No. 5, the number of cfus prior to installation were 212 at the handpiece A and 89,500 at the water irrigation implement. Thereafter and for the next five weeks, the number of cfus at each of the handpiece and the water irrigation implement was essentially zero. In office No. 6, handpiece A contained 4,100 cfus and the water irrigation implement contained 350 cfus prior to the installation of the present invention. After installation and one week thereafter, the cfus at both locations dropped to zero.

Accordingly, one must come to the inescapable conclusion that the present invention is highly effective in destroying microorganisms in the environment of a dental operatory. Furthermore, it will destroy any existing biofilm and will prevent the buildup of biofilm in the attendant water conduits and water conveying and pieces and implements used in the dental practice.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention.

What is claimed is:

1. A method for destroying microorganisms and biofilm within conduits conveying water from a container to dental handpieces and water discharging implements and within any of the channels of the handpieces and of the implements by oxidizing any microorganisms and biofilm present, said method comprising the steps of:

(a) providing a source of oxygen containing gas under pressure in the range of about 30 PSIG to about 40 PSIG;

(b) generating ozone from the gas under pressure with a UV opaque member to produce ozone enriched gas, and step of generating being performed within the container using an ozone generator;

(c) conveying the ozone enriched gas into the water within the container, which water is to be directed to the handpieces and implements and to pressurize the water at a pressure above ambient pressure;

(d) entraining the ozone enriched gas in the water in the container to produce ozone enriched water;

(e) further conveying the ozone enriched water through the conduits to a silver catalyst cartridge to attract the oxygen to the silver and cause the oxygen to dissociate from its normal diatomic state to bond with the silver;

(f) oxidizing the microorganisms with oxygen dissociated from the silver; and (g) dissolving silver into the water flowing downstream of the silver catalyst cartridge through the conduits to permit adherence of the silver to the water conveying surfaces of the conduits, handpieces and implements and subsequent reaction with oxygen in the water to oxidize any attendant microorganisms and biofilm.

2. The method as set forth in claim 1 wherein said step of conveying and entraining are performed within the container.

3. The method as set forth in claim 1 including the step of enriching with oxygen the gas to be ozone enriched.

4. The method as set forth in claim 1 wherein said step of generating comprises the step of urging flow of the oxygen containing gas past a source of ultraviolet radiation.

5. The method as set forth in claim 4 wherein the container includes a cap for sealing the container and including the step of supporting the ozone generator from the cap.

6. Apparatus for entraining ozone in a fluid to be delivered to a water manifold and associated conduits in fluid communication with dental implements to oxidize organic matter and microorganisms that may be present in the fluid, and to destroy biofilm present on the surface of the conduits and on the water conveying surfaces of the dental implements, and apparatus comprising in combination:

(a) an ozone generator for generating ozone comprising a source of UV radiation, a member for housing said UV radiation source, said member being opaque to UV radiation and able to withstand about 30 psig pressure;

(b) a source in fluid communication with said member for conveying an oxygen containing gas under pressure into said member to accommodate ozone generation under pressure in said ozone generator;

(c) a pressurizable container of the fluid to be ozonated to provide a source of ozonated fluid through a port to the manifold, the conduits and the dental implements, and ozone generator being disposed within said container;

(d) a device disposed in said container and in fluid communication with said ozone generator for entraining the ozone and the gas from said ozone generator under pressure in the fluid within said container to enhance the level of ozone concentration in the fluid and to provide the source of ozonated fluid;

(e) a silver catalyst cartridge in fluid communication with said container for receiving the ozonated fluid to weakly bond oxygen radicals with the silver and result in subsequent dissociation of the oxygen radicals from the silver to oxidize organic matter and microorganisms in contact therewith and for dissolving silver into the ozonated water to permit adherence of the silver to the interior surfaces of the manifold, the conduits and the dental implements to react with oxygen in the water and further oxidize organic matter and microorganisms; and (f) an outlet of said silver catalyst cartridge in fluid communication with the manifold, the conduits and the dental implements to interconnect said outlet with the manifold, the conduits and the dental implements to convey the ozonated fluid and silver to the manifold, the conduits and the dental implements.

7. The apparatus as set forth in claim 6 wherein the pressure within said container is from about 30 to about 40 psig.

8. The apparatus as set forth in claim 6 wherein said entraining device is a sparger.

9. The apparatus as set forth in claim 6 wherein the pressure within said container is from about 30 PSIG to about 40 PSIG.

* * * * *